United States Patent [19]

Hempel et al.

[11] 4,176,127

[45] Nov. 27, 1979

[54] PROCESS FOR THE PRODUCTION OF SILANES FROM OLEIC ACID ESTERS

[75] Inventors: Hans-Ulrich Hempel, Overath Vilkerath; Hans-Jürgen Klüeppel; Peter Volgnandt, both of Düsseldorf, all of Fed. Rep. of Germany

[73] Assignee: Henkel Kommanditgesellschaft auf Aktien (Henkel KGaA), Dusseldorf-Holthausen, Fed. Rep. of Germany

[21] Appl. No.: 959,944

[22] Filed: Nov. 13, 1978

[30] Foreign Application Priority Data

Nov. 28, 1977 [DE] Fed. Rep. of Germany ....... 2752973
Aug. 17, 1978 [DE] Fed. Rep. of Germany ....... 2836054

[51] Int. Cl.$^2$ .......................... C08H 3/00; C07F 7/02
[52] U.S. Cl. ................................. 260/407; 260/408; 260/409; 260/448.2 E
[58] Field of Search ......... 260/407, 408, 409, 448.2 E

[56] References Cited

U.S. PATENT DOCUMENTS

| | | | |
|---|---|---|---|
| 2,524,529 | 10/1950 | Krieble | 260/448.2 E |
| 2,823,218 | 2/1958 | Speier | 260/448.2 E |
| 2,948,742 | 8/1960 | Zajcew | 260/409 |
| 3,507,890 | 4/1970 | Dieckelmann | 260/407 |
| 3,950,365 | 4/1976 | Singer et al. | 260/407 |

*Primary Examiner*—John F. Niebling
*Attorney, Agent, or Firm*—Hammond & Littell

[57] ABSTRACT

In the process for the production of a long chain silane consisting essentially of reacting a hydrogen silane with a commercial oleic acid ester with a lower alkanol in the presence of a catalyst, at a temperature above 50° C. and recovering said long chain silane, the improvement consisting essentially of utilizing a commercial oleic acid ester with a lower alkanol containing less than 4% by weight of poly-unsaturated compounds, as said oleic acid ester.

8 Claims, No Drawings

PROCESS FOR THE PRODUCTION OF SILANES FROM OLEIC ACID ESTERS

BACKGROUND OF THE INVENTION

It is known to prepare silanes by reacting oleic acid esters or corresponding esters of linoleic acid with hydrogen silanes, at temperatures above 50° C., in the presence of a catalyst. As catalysts there have been proposed in particular platinum or chloroplatinic acid, azo compounds, organo metallic compounds and peroxides. Particularly high yields are said to have been obtained in the presence of chloroplatinic acid.

However, when commercial oleic acid esters, such as those obtained from olein, tallow oil or tall oil are used, the yields obtained from the reaction with silanes are poor, and frequently below 30%.

OBJECTS OF THE INVENTION

An object of the present invention is the development of a process for the production of silanes from commerical oleic acid esters with high yields.

Another object of the present invention is the improvement in the process for the production of a long chain silane consisting essentially of reacting a hydrogen silane with a commercial oleic acid ester with a lower alkanol in the presence of a catalyst at a temperature above 50° C., and recovering said long chain silane, the said improvement consisting essentially of utilizing a commerical oleic acid ester with a lower alkanol containing less than 4% by weight of poly-unsaturated compounds, as said oleic acid ester.

These and other objects of the present invention will become apparent as the description thereof proceeds.

DESCRIPTION OF THE INVENTION

It has now been found that silanes are obtained in high yields from commerical oleic acid esters with lower alkanols by their reaction with hydrogen silanes in the presence of a catalyst at temperatures above 50° C., if the commercial oleic esters contain less than 4% by weight of poly-unsaturated compounds. If the commercial oleic acid esters with lower alkanols contain more than 4% of poly-unsaturated compounds, this proportion can be reduced to below 4% by known methods.

More particularly, therefore, the present invention relates to an improvement in the process for the production of a long chain silane consisting essentially of reacting a hydrogen silane with a commercial oleic acid ester with a lower alkanol in the presence of a catalyst, at a temperature above 50° C. and recovering said long chain silane, the said improvement consisting essentially of utilizing a commercial oleic acid ester with a lower alkanol containing less than 4% by weight of poly-unsaturated compounds, as said oleic acid ester.

The proportion of poly-unsaturated compounds in the commercial oleic acid esters with lower alkanols may be reduced by dimerizing the poly-unsaturated compounds present in the commercial oleic acid ester. Such dimerization may be carried out in the presence of a Fuller's earth catalyst of the montmorillonite type, having a specific surface area greater than 150 m²/gm, preferably from 200 to 250 m²/gm, using temperatures of from 110° to 210° C., preferably from 140° to 180° C. The catalysts are utilized in an amount of from 5% to 20% by weight, based on the fatty acid and fatty acid ester mixture. The treatment time is approximately from one to four hours. The dimerized products may be subsequently separated from the oleic acid esters by distillation but such separation is not always necessary.

The reduction in the proportion of poly-unsaturated compounds in commercial oleic acid esters with lower alkanols to the level indicated above may also be carried out by treatment of the esters in the presence of macroporous ion exchange resins without a gel character, which have a high specific surface area of about 40 m²/gm and a pore size of approximately 250 to 300 Å, by heating the ester mixture with the ion exchange resin to temperatures in the range of from 90° to 140° C. Catalysts of this type are available commercially, for example, under the trade name of "Amberlyst 15" ®. The catalysts are used in quantities of from 3% to 10% by weight, based on the fatty acid or fatty acid ester mixture.

An alternative method for reducing the proportion of poly-unsaturated compounds in the commercial oleic acid esters with lower alkanols to the required level consists of partially hydrogenating the commercial oleic acid ester, that is to say, to a degree of hydrogenation of approximately 5% to 25%.

This partial hydrogenation may be carried out by, for example, hydrogenating the methyl or other lower alkyl ester of oleic acid in the presence of platinum, active charcoal, Raney nickel, palladium or other known hydrogenation catalysts.

The reaction of the commercial oleic acid ester with lower alkanols, now containing less than 4% by weight of poly-unsaturated compounds, with the hydrogen silane is suitably carried out in the presence of organic peroxides as catalysts. Suitable peroxides for this purpose are, in particular, benzoyl peroxide and di-tert.-butyl peroxide. The catalysts are used in the usual quantities of about 0.05% to 5% by weight, preferably 1% to 4% by weight, based on the fatty acid ester mixture. Suitable hydrogen silanes include, in particular, trichlorosilane, dimethylchlorosilane and methyldichlorosilane.

It is advantageous although not essential to use an excess of hydrogen silane when carrying out this reaction. The excess may, for example, amount to about 0.5 to 2 mols, based on the quantity of oleic ester used.

The reaction is carried out at temperatures of from 50° to 150° C., preferably from 90° to 110° C., but if temperatures below 85° C. are employed, the reaction time is increased accordingly.

The reaction products obtained are worked up by separating the reaction mixture into its individual components by distillation at reduced pressure, whereby unreacted silane and esters are recovered.

The products, i.e., illustrated by the example of the reaction of methyl oleate with trichlorosilane, correspond to the following formulae:

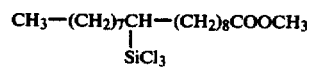

or

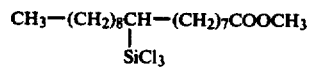

The products obtained may be used as hardeners in binders based on alkali metal silicates and as additives to antistatic agents, plasticizers and adhesives.

The commercial oleic acid esters with lower alkanols, particularly methanol will vary in composition depending on the source. Customarily, however, they will contain 55% to 95% of esters. The esters can contain from about 0.5% to 14% by weight of saturated acid esters, mainly stearic acid ester, 60% to 85% by weight of oleic acid ester and from 4.1% to 15% be weight of poly-unsaturated acid esters, mainly linoleic acid ester.

The subject of the application will now be explained with the aid of the following examples, in which the following abbreviations are used:

$C_{18}S$ = Stearic acid
$C_{18:1}$ = Oleic acid
$C_{18:2}$ = Linoleic acid

EXAMPLE 1

(a) Hydrogenation of the Starting Material

Commercial methyl oleate having the composition:
$C_{18}S$ = 0.9%
$C_{18:1}$ = 76.6%
$C_{18:2}$ = 4.3% was hydrogenated, using platinum on active charcoal as catalyst. Hydrogenation was stopped when the composition was:
$C_{18}S$ = 6.3%
$C_{18:1}$ = 72.0%
$C_{18:2}$ = 2.3%

This corresponds to a partial hydrogenation of approximately 5%, based on the methyl oleate content. The fatty acid ester mixture obtained was separated from the catalyst and used for silylation.

(b) Reaction with Trichlorosilane

Reaction Mixture:
150 gm of fatty acid ester mixture described above containing 108 gm of methyl oleate (0.38 mol), 101 gm of trichlorosilane (0.75 mol) and 4 gm of dibenzoyl peroxide.

The ester mixture and dried dibenzoyl peroxide were mixed with trichlorosilane under a nitrogen atmosphere at room temperature. The mixture was then heated slowly. A temperature of 85° C. was reached after eleven hours. After the addition of a further 2 gm of peroxide, the temperature rose rapidly to 110° C. After removal of the excess trichlorosilane by distillation, the product was worked up by fractional distillation in a high vacuum.

Boiling Point: 155° to 158° C. at 0.01 Torr
Yield: 151 gm (0.35 mol)—92% of the theoretical.

(c) Reaction Without Previous Partial Hydrogenation

When commercial methyl oleate of the composition indicated under (a) was reacted with trichlorosilane by the same method as described under (b) but without previous partial hydrogenation, the yield obtained was approximately 24%.

EXAMPLE 2

200 gm of methyl oleate prepared from tall oil was hydrogenated as described in Example 1. Hydrogenation was stopped at a composition of:
$C_{18}S$ = 23.3%
$C_{18:1}$ = 37.8%
$C_{18:2}$ = approximately 1%.

This corresponds to a partial hydrogenation of 20%, based on the methyl acid ester content. After removal of the catalyst, 0.27 mol of the methyl acid ester obtained were mixed with 60 gm of trichlorosilane (0.44 mol) and 3 gm of benzoyl peroxide and the mixture was slowly heated to reflux with stirring. The temperature rose from 70° C. to 150° C. within two hours. The reaction mixture was distilled in a high vacuum. The yield of oleic acid methyl ester trichlorosilane was 72 gm (62%).

EXAMPLE 3

Commercial methyl oleate containing 72% of oleic acid, 7% of linoleic acid and 11% of methyl esters of saturated fatty acids having 14 to 18 carbon atoms was heated for two hours at 160° C. in the presence of 10% of Fuller's earth catalyst of the montmorillonite type (commercial product "Tonsil LFF 80" ®). The fatty acid ester mixture obtained was separated from the catalyst and used for silylation. The proportion of linoleic acid in the fatty acid ester mixture had fallen to 3.2%.

The reaction with trichlorosilane was carried out as described in Example 1, paragraph (b). The yield was 144 gm = 87% of the theoretical yield.

EXAMPLE 4

A commercial methyl oleate consisting of 74% of oleic acid, 10% of methyl esters of poly-unsaturated fatty acids and residues of methyl esters of saturated monomeric fatty acids was heated to 120° C. for three hours in the presence of an acid macroporous ion exchange resin without gel character (trade product "Amberlyst-15" ®). Analysis showed that at the end of this time, the reaction product contained only 1% of esters of poly-unsaturated fatty acids. After removal of the catalyst from the fatty acid ester mixture, silylation was carried out as described in Example 1, paragraph (b). The yield was 147 gm = 89% of the theoretical yield.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. In the process for the production of a long chain silane consisting essentially of reacting a hydrogen silane with a commercial oleic acid ester with a lower alkanol in the presence of a catalyst at a temperature above 50° C. and recovering said long chain silane, the improvement consisting essentially of utilizing a commercial oleic acid ester with a lower alkanol containing less than 4% by weight to poly-unsaturated compounds, as said oleic acid ester.

2. The process of claim 1 wherein said commercial oleic acid ester with a lower alkanol containing less than 4% by weight of poly-unsaturated compounds was derived from a commercial oleic acid ester with a lower alkanol having over 4.1% of poly-unsaturated compounds.

3. The process of claims 1 or 2 wherein the proportion of poly-unsaturated compounds in said commercial oleic acid ester with a lower alkanol was reduced by dimerization of these compounds.

4. The process of claim 3 wherein said dimerization is conducted in the presence of Fuller's earth.

5. The process of claim 3 wherein said dimerization is conducted in the presence of an ion exchange resin.

6. The process of claims 1 or 2 wherein the proportion of poly-unsaturated compounds in said commercial oleic acid ester with a lower alkanol was reduced by partial hydrogenation to a degree of from 5% to 25%.

7. The process of claim 1 wherein said catalyst is an organic peroxide.

8. The process of claim 1 wherein said temperature is from 50° C. to 150° C.

* * * * *